United States Patent [19]

Ikeda

[11] Patent Number: 4,994,056

[45] Date of Patent: Feb. 19, 1991

[54] UNIT DOSE MEDICAMENT STORING AND MIXING SYSTEM

[76] Inventor: Daniel P. Ikeda, 6436 Harmon Dr., Sacramento, Calif. 95831

[21] Appl. No.: 434,010

[22] Filed: Nov. 9, 1989

[51] Int. Cl.[5] .............. A61B 19/00

[52] U.S. Cl. .............. 604/410; 604/87; 206/221

[58] Field of Search .............. 206/219, 220, 221, 222; 383/38–40; 604/410, 82, 85, 89, 92

[56] References Cited

U.S. PATENT DOCUMENTS

| | | | |
|---|---|---|---|
| 2,916,197 | 12/1959 | Detrie et al. | 206/221 X |
| 3,149,943 | 9/1964 | Amador | 206/221 X |
| 3,257,072 | 6/1966 | Reynolds | 206/47 A |
| 3,809,224 | 5/1974 | Greenwood | 206/219 |
| 4,401,214 | 8/1983 | Kleckers | 206/219 |
| 4,519,499 | 5/1985 | Stone et al. | 206/219 |
| 4,608,043 | 8/1986 | Larkin | 604/87 |
| 4,610,684 | 9/1986 | Knox et al. | 604/416 |
| 4,629,080 | 12/1986 | Carveth | 215/11 R |
| 4,630,727 | 12/1986 | Feriani et al. | 206/221 |
| 4,632,244 | 12/1986 | Landau | 206/219 |
| 4,637,061 | 1/1987 | Riese | 383/38 |
| 4,711,359 | 12/1987 | White et al. | 215/11.1 |
| 4,770,295 | 9/1988 | Carveth et al. | 206/219 |
| 4,787,511 | 11/1988 | McIver | 206/219 |

OTHER PUBLICATIONS

Abbott Laboratories promotional material 3/88 "Aminosyn Bag".

*Primary Examiner*—Robert A. Hafer
*Assistant Examiner*—Lynda M. Cofsky
*Attorney, Agent, or Firm*—Oliff & Berridge

[57] ABSTRACT

A unit dose medicament storing and mixing system is described having a dual compartmented and collapsible container for use in an intravenous administration system. One of the compartments contains unit dose measurements of sterile medicament (in powder or liquid form), the second compartment to contain sterile intravenous fluid to be used as a diluent. The two compartments are separated by a closure which is separable and resealable. An external clamping device is used to lock the resealable closure and keep the compartments separate. Prior to the infusion of the activated medicament to the patient, the drug is prepared by removing the external clamp and separating the resealable membrane device, thereby providing fluid communication between chambers and effecting intermixing of the contents thereof. The membrane can then optionally be resealed in order to separate the medicament to be delivered from any residual air left in the container.

12 Claims, 4 Drawing Sheets

UNIT DOSE MEDICAMENT STORING AND MIXING SYSTEM

FIELD OF THE INVENTION

This invention relates to medicament delivery systems, particularly ones in which a premeasured amount of medicament is to be mixed at the time of use with a diluent and delivered by intravenous infusion.

BACKGROUND OF THE INVENTION

Intravenous medications are given in standardized doses as indicated by the pharmaceutical manufacturer. Currently these standardized doses of medicament are compounded and mixed in intravenous fluid, ideally in a laminar flow hood to limit possible contamination, by one licensed and skilled in the art, prior to delivery of the medicament to a patient. Following mixing, the medicament has only a finite life in its active form depending upon the individual drug (generally one day to one week at room temperature) and must be used within this period after which the medicament loses its activity and must be discarded.

Once mixed and prior to its infusion free air must be removed from the mixing and storage container so as to prevent the inadvertent delivery of free air into a patient's vein with resultant harmful consequences.

Container devices providing separate compartments in a single unit for separately enclosing incompatible materials in such a way that they may be later intermixed are described in U.S. Pat. No. 2,176,923 to Nitardy, U.S. Pat. No. 3,290,017 to Davies, et al., U.S. Pat. No. 3,532,254 to Burke, et al., U.S. Pat. No. 3,608,709 to Pike and U.S. Pat. No. 4,637,061 to Riese. These container devices are not believed to be able to maintain an effective fluid-tight seal or moisture barrier between the various spaces formed within the container for the purposes of preparation and storage of sterile medications. This is caused by the various barriers between the spaces not adequately withstanding the normal rigors of packaging, handling and shipping. If the fluid-tight seal or moisture barrier between the storage spaces is broken, premature mixing of the materials may occur which then renders them ineffective for eventual use. Additionally, for containers used in health care situations, sterility of the materials to be mixed must be strictly maintained.

Container devices are described in U.S. Pat. No. 4,458,811 to Wilkinson and U.S. Pat. No. 4,608,043 to Larkin. In these devices designed for intravenous fluid storage and mixing, there is employed a system designed around a central partition with a weakened portion that is frangible with direct external compression. Upon rupture of the weakened portion, the medicament is mixed with the diluent. Uncertainty exists as to the integrity of the weakened portion in the partition so as to guarantee a fluid-tight seal or moisture barrier that will withstand both the rigors of storage and handling, yet allow the weakened portion to be easily broken. There is also a question whether a sufficiently large opening is formed in the frangible section to allow easy mixing of substantially all of a powdered medicament with the diluent liquid. This stems from the fact that the requirements for such a seal are mutually incompatible. A strong seal is needed to prevent moisture transfer and to enable the seal to withstand the rigors of handling and storage. Yet the seal must be easily rupturable to form an opening large enough to allow complete intermixing of the components. Further, in these designs, any air or other gas within the container cannot be separated from the medicament infusion fluid after mixture.

SUMMARY OF THE INVENTION

The present invention relates to a manually operable dual chambered container which includes the means to separately store and mix, under sterile conditions, the contents of the two chambers by manipulation from outside the container. More particularly, this invention provides a mixing and storage system for use in the infusion of intravenous liquids. The mixing system is made a part of a single, flexible container used to hold a standard liquid diluent, such as normal saline solution, dextrose or water. The additive is commonly a powdered or liquid medicament which is compatible with the liquid diluent for treatment purposes but cannot be stored in solution with the liquid diluent for long periods of time.

The dual chambered container includes an internal seal member openable and closable from the outside of the container. An external clamp is positionable across the sealing member. The clamp includes sealing surfaces for augmenting the seal formed by the sealing member both during storage and after mixture of the medicament and diluent.

This invention relates to storing, mixing and delivery of a unit dose of medicament for intravenous infusion. The invention provides a totally closed environment, allowing for complete separation of sterile medicament and diluent until activation of the drug is initiated by removal of the external clamp and separation of the membrane dividing the two compartments. After mixing, free air can be segregated from the medicament and the preparation can be directly administered to a patient using an intravenous administration system. Its major attributes will allow for the mass storage of unit dose preparations at room temperature, preserving activity. This invention is designed to reduce potential contamination that can be incurred by manual preparation of drugs for infusion. In its preferred form the storage device is made of flexible plastic that can be effectively sterilized, which at one end contains a compartment filled with sterile medicament in the form of powder or liquid, and at the other end a compartment containing intravenous diluent appropriate for the medicament it is packaged with. The preferred embodiment has a separable closure between the two compartments which is composed of parallel mating protrusions with two centrally located tabs on the external surface of the device to be used to separate the closure.

It is an object of the present invention to provide a container for maintaining ingredients separated during storage and for effecting complete mixing thereof at the time of use.

It is another object of the present invention to provide two separate mechanisms of compartmental separation, an internal interlocking and resealable membrane and an external protective clamp, guaranteeing the integrity of a fluid-tight seal or moisture barrier to an extent necessary to satisfy federal drug regulatory requirements and designed to withstand the rigors of storage and handling.

It is an object advantage of the present invention to provide an infusion container with a resealable fluid-tight seal, in order to separate and thereby remove any free air residing within the container from the activated medication prior to delivery of the medication to the patient.

It is a further object of the present invention to provide a closed system for the preparation of sterile medicaments and intravenous solution so as to prevent potential mixing errors and contamination of the sterile environment during the mixing and compounding process.

It is still a further object to provide a container having the foregoing features which is inexpensive to manufacture.

It is a further object of the invention to reduce the cost of and time necessary for preparing and handling intravenous medications.

It is a further object of the invention to increase the safety of and reduce the chances for contamination of intravenous medications.

DESCRIPTION OF THE DRAWINGS

A better understanding of the storage and mixing device will the had by reference to the drawings wherein.

DESCRIPTION OF THE PREFERRED EMBODIMENT

Figure 1:
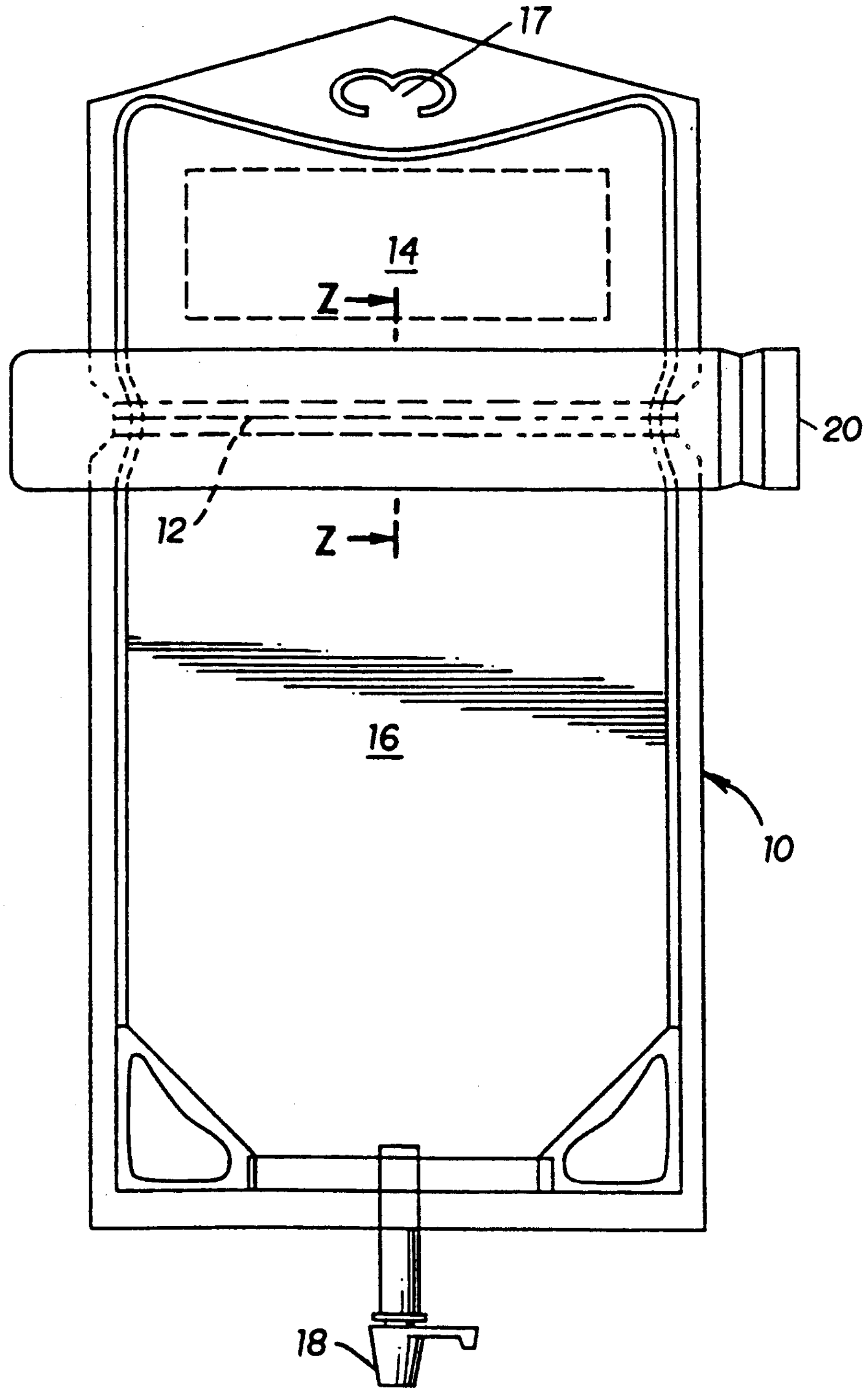
FIG. 1 is a view in front elevation of the storage and mixing device of this invention with external clamp attached.

While this invention is susceptible to embodiment in many different forms, there is shown in the drawings and will herein be described in detail, a specific embodiment, with the understanding that the present disclosure is to be considered as an exemplification of the principle of a unit dose medicament storage, mixing and delivery preparation, and is not intended to limit the invention to the embodiment illustrated.

Referring to FIG. 1 of the drawing, the flexible compartmentalized container generally includes a tubular body 10 formed of a heat sealable, fluid impervious, polymeric material. The body 10 is sealed along its four edges to form a bag-like structure.

The bag includes at least one intravenous administration port, such as port 18, in fluid communication with compartment 16. The port 18 may be sealed to the bag by the bottom seal. The port is of a conventional type commonly used for this purpose. Other ports, such as additional administration ports or addition ports (not shown) can be placed, in like manner, in the bag.

Extending transversely between the side edges of the bag is a separable and resealable closure 12, which, when closed, forms two fluid-tight compartments 14 and 16 at upper and lower portions of bag 10, respectively. The compartments 14 and 16 are filled at the time of manufacture with separate ingredients which, during storage, are kept separated but immediately before use are mixed. For example, a unit dose of a medicament in powder or liquid form may be contained in compartment 14, and an infusible diluent is stored in compartment 16. If either or both of the substances in compartments 14 and 16 are subject to degradation by light exposure, an opaque liner is provided in the appropriate compartment to retard such degradation.

An external clamp 20 which extends over front and rear surfaces 22 and 24 (FIG. 2), respectively, of the bag is retained on the bag. The clamp is placed over the closure 12, as will hereinafter be described.

A mounting hole 17 is provided in a top edge of the bag 10. The hole 17 provides a means for hanging the bag 10 from a stand.

Figure 2:
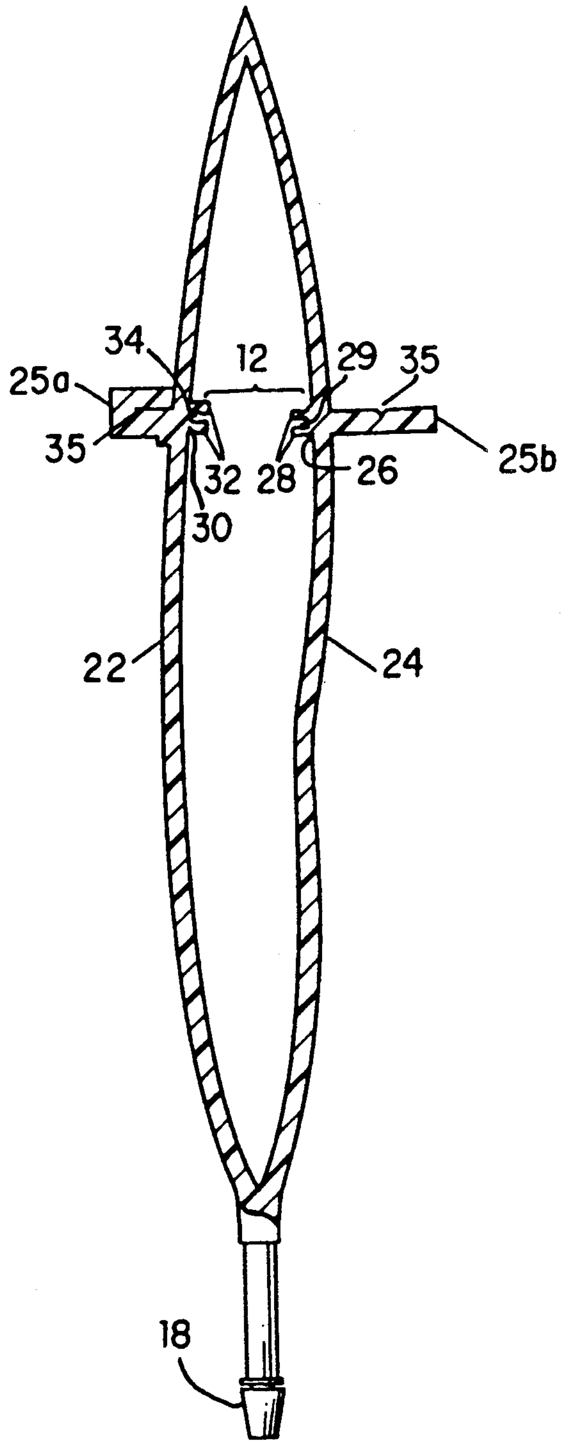
FIG. 2 is a view in side cross-sectional view of the storage and mixing device of this invention without the external clamp attached.
Figure 3:
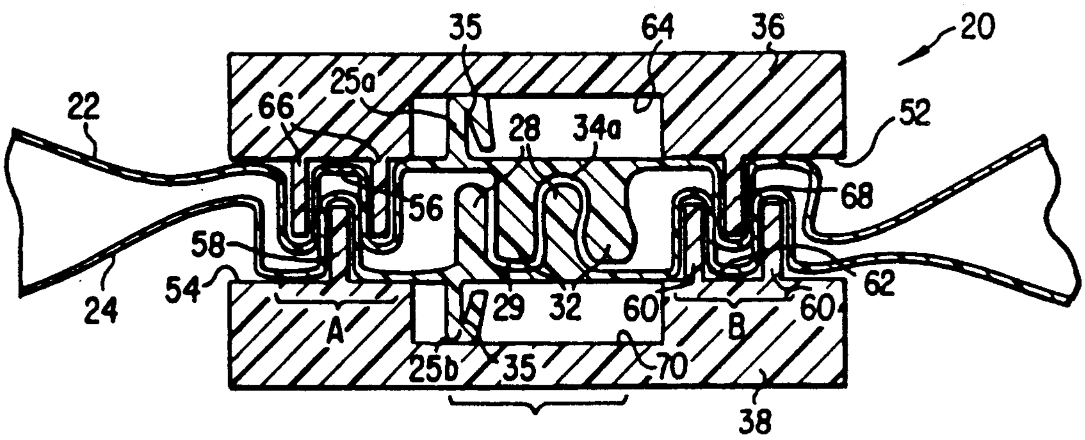
FIG. 3 is a partial sectional view taken along line Z—Z of FIG. 1.
Figure 4:
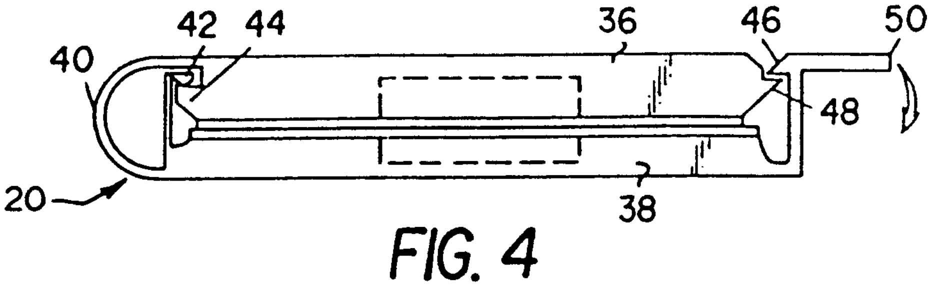
FIG. 4 is a side view of the external clamp in locked position.

The separable closure is illustrated in FIGS. 2 and 3. The separable closure 12 is generally rectangular and flat in configuration with opposing and overlapping mating portions A first mating portion 26 comprises two parallel, upstanding transversely extending locking ridges 28. A second mating portion 30 includes two parallel, upstanding transversely extending ridges 32. The ridges 28 and ridges 32 are aligned to interlock and form a fluid light seal. To achieve this, ridges 32 form between them a groove 34 adapted to tightly receive one of the ridges 28 and form a fluid sealing relationship therewith. Similarly, a groove 29 is formed between ridges 28 to receive one of the ridges 32. The material of the closure portions is flexible so that pressure on the outside surfaces of a closure 12 will cause the two mating portions to interlock and hold the container in a liquid-tight condition thereby defining the two compartments 14 and 16 shown in FIG. 1. Both mating portions 26 and 30 of the container 10 are integral parts of two opposed rectangular strips of material (not shown) which carry the ridges 28 and ridges 32, respectively. While FIGS. 2 and 3 shows each mating portion of closure 12 to include two generally semi-circular sealing surfaces, it will be understood that other configurations may be used.

Referring to FIG. 2, on member 10 there are two tabs 22 and 24. The tabs are slightly offset and hinged, as at 35, to allow for folding as depicted by tab 25*a* in FIG. 2 and both the tabs 25*a* and 25*b* in FIG. 3. The tabs 25*a*, 25*b* provide for separation of closure 12, allowing the contents of compartment 14 to mix with the intravenous fluid diluent stored in compartment 16.

Figure 5:
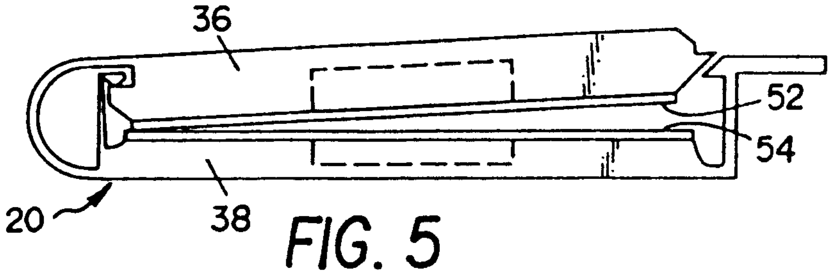
FIG. 5 is a side view of the clamp in unlocked condition.
Figure 6:
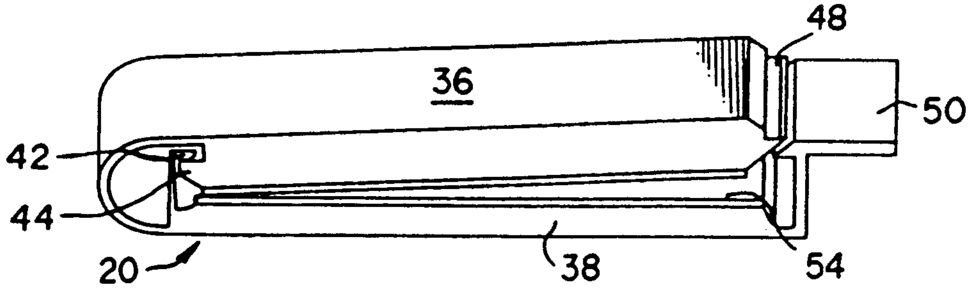
FIG. 6 is a perspective view of the clamp.

External to the bag 10 and secured across closure 12 is an external protective clamp 20 that overlies the separable closure to act as a dual lock to prevent premature separation of member 12, prior to the desired activation of a drug that is packaged within. Referring to FIGS. 3 and 4–8, the external clamp 20 comprises an integral molded plastic unit with a top section 36 and a bottom section 38. At one end is a curved connecting band of plastic 40 that provides a natural spring that tends to open the clamp. Tang 42 and boss 44 form an interlocking joint which provides a hinge and a locking point at one end of the clamp. The other end of the clamp is interlocked by opposing tangs 46 and 48. Downward pressure on tab 50 will release the tangs 46 and 48 allowing the clamp to be opened, as illustrated in FIG. 5, and removed from bag 10.

Figure 7:
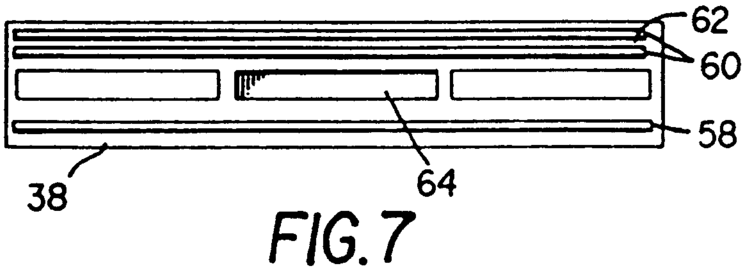
FIG. 7 is a plan view of one of two mating surfaces of the clamp.
Figure 8:
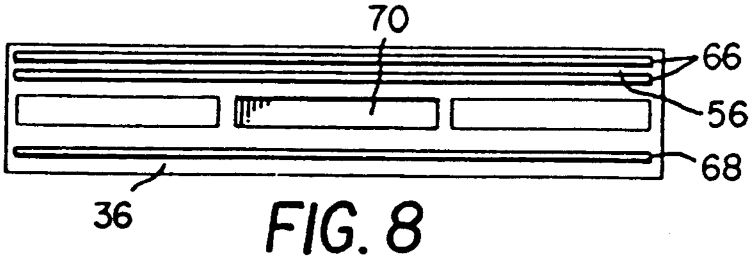
FIG. 8 is a plan view of a second mating surface of the clamp.

As shown in FIGS. 3 and 5, the clamp 20 includes opposed flat clamping surfaces 52 and 54 on top member 36 and bottom member 38, respectively. As shown in FIGS. 3 and 7, on the surface 54 of section 38 are two parallel upstanding ribs 60 along one edge thereof, forming a groove 62 therebetween. Along the other edge of surface 54 is a rib 58. Along one edge of the flat surface 52 of section 36 are two parallel ribs 66 forming between them a groove 56. Along the other edge of the surface 52 is a rib 68. The ribs 58 and 68 are arranged to protrude within grooves 56 and 62 formed between the pairs of ribs 66 and 60, respectively, as shown.

In the center of section 38 there is a hollow depression 70 that is sized to receive one of the tabs, for example tab **25*b*. In the center of section 36 there is a hollow depression 64 that is designed to snugly fit the other one of the tabs, 25*a*. The enclosure of the tabs 25*a*, 25*b* within the clamp lessens the likelihood of inadvertent separation of the closure 12** during storage or handling.

FIG. 3 depicts a cross section of closure 12 with structures 28 and 32 interlocked and the external clamp 20 attached and secured. Compartments 14 and 16 are separated and effectively externally sealed off by compression of the clamp 20 at points A and B, to form labyrinth-type seals between sheets 22 and 24 on each side of closure 12 and are internally sealed by the separable closure 12.

Within the container as described above, a predetermined unit-dose quantity of sterile medicament in powder or liquid form is deposited under sterile conditions into the compartment 14 during manufacture and thermally sealed. An appropriate volume of intravenous diluent is stored in compartment 16. When it is desired to activate this unit dose preparation, the protective external clamp 20 is removed. The two tabs **25*a* and 25*b* are held and pulled in opposite directions, thereby breaking the seal separating compartments 14 and 16. The medicament is then mixed thoroughly with this intravenous diluent and, upon completion of mixing, the medicament is activated and ready to be delivered to the patient intravenously. Because the closure 12 can be opened completely between side edges of bag 10, there can be thorough mixing of diluent within compartment 14 and, conversely, a complete release of a powdered medicament into the compartment 16. The resealable closure 12 can now be partially resealed by finger pressure applied to opposite external surfaces of bag 10 in the region of closure 12. Any free air that resides within the mixing chamber can now be separated from the activated drug by pressure on the lower portion of the compartment 16, forcing free air through the partially closed closure 12 into compartment 14. Complete closure of the resealable membrane 12 can then be performed to provide a barrier between the activated medication and residual air. For additional safety, the external clamp 20 can also be secured over the closure 12 to prevent accidental opening of closure. A bag spike can now be inserted into the male port 5 and the medication can be infused into the patient by gravity or by infusion pump. The bag may be hung via hole 17** for engagement with the usual support hook (not shown).

If the bag 10 is to be used in conjunction with a syringe pump device, a syringe port (not shown) is provided. A syringe with needle is inserted through the syringe port and the prepared solution is withdrawn. The filled syringe is then attached to a syringe pump device for infusion of the drug into the patient.

The preferred plastic resin for plastic sheet material forming the bag 10 is a polyolefin. Other usable thermoplastic resinous materials are polyvinylchloride and polyester, depending upon the type of materials to be placed in the bags and the sterilization thereof.

While the present storage and mixing system has been preferably described for use with a liquid diluent and a powdered medicament, the system may be used with liquids in both chambers. Further, while the present storage and mixing system has been described for use in the health care field, it will be appreciated that the system can be used in other fields. For example, it might have application with other incompatible fluid materials where it is necessary to maintain the two fluid materials in a separately stored and isolated condition until a time just prior to their mixing and use. It should be understood that the term "fluid" as employed in the specification and claims is meant to imply any materials which will flow from one container to another, whether solid, liquid, or gas.

It will be seen through the present invention there is now provided a storage and mixing system which is easily manufactured and used. The container system of this invention affords a sterile environment for fluid materials of any type during a storage as well as mixing, yet in a manner that provides an inexpensive system for the user.

The foregoing invention can now be practiced by those skilled in the art. Such skilled persons will know that the invention is not necessarily restricted to the particular embodiments presented herein. The scope of the invention is to be defined by the terms of the following claims, as given meaning by the preceding description.

What is claimed is:

1. A package for separately storing and subsequently mixing two ingredients comprising:

a container formed of first and second opposed walls of flexible material and having at least one port;

a closure dividing said container to define first and second compartments within said container, the closure being formed by at least one leak-proof, resealable interior fastener disposed between a top and a bottom of said container, the interior fastener having a first mating portion and a second mating portion, the first mating portion being disposed on the inner surface of the first wall of the container, and the second mating portion being disposed on the inner surface of the second wall opposite the first mating portion; and an external clamp to fit over the closure, said external clamp including means for forming first and second external seals between the first and second walls of the container, the first external seal being disposed on one side of the closure and the second external seal being disposed on the other side of the closure.

2. The package of claim 1 wherein first mating portion includes a pair of parallel protrusions forming a groove therebetween and the second mating portion includes a protrusion aligned with the groove and configured for resilient, locking engagement therewith.

3. The package of claim 1 having gripping means attached to the outer surfaces of said first and second walls for opening of said interior fastener.

4. The package of claim 3 wherein each gripping means comprises a rectangular strip of material having a longitudinal edge affixed to a wall parallel to an associated mating portion of the interior fastener.

5. The package as in claim 3 wherein the clamp includes means for receiving the gripping means.

6. The package as defined in claim 1, wherein said port is in fluid communication with said first chamber.

7. The package as defined in claim 6 wherein the port is adapted to receive connecting means for connecting the container to an intravenous administration set.

8. The package as defined in claim 1 wherein one chamber contains a liquid diluent and the other chamber contains a powdered medicament.

9. The package as in claim 1 wherein the closure is substantially linear and the first and second external seals are substantially parallel to and coextensive with the closure.

10. The package as in claim 9 wherein the first and second seals are labyrinth seals.

11. A container as in claim 1 wherein the external seals are labyrinth seals.

12. A container as in claim 1 wherein the container comprises a bag having opposed side edges and wherein the closure extends transversely between the side edges.

* * * * *

UNITED STATES PATENT AND TRADEMARK OFFICE

CERTIFICATE OF CORRECTION

PATENT NO. : 4,994,056

DATED : February 19, 1991

INVENTOR(S) : Daniel P. Ikeda

It is certified that error appears in the above-identified patent and that said Letters Patent is hereby corrected as shown below:

Column 6, claim 1, line 5, after "container" insert --, said closure extending across the interior of said container".

Column 8, claim 11, line 1, change "A container" to --The package--.

Signed and Sealed this

Fourth Day of May, 1993

Attest:

Michael K. Kirk

MICHAEL K. KIRK

*Attesting Officer*

*Acting Commissioner of Patents and Trademarks*